US00PP30295P2

(12) United States Plant Patent
Widdowson

(10) Patent No.: US PP30,295 P2
(45) Date of Patent: Mar. 12, 2019

(54) ***GAURA* PLANT NAMED 'SUMMER STAR BABY'**

(50) Latin Name: *Gaura lindheimeri*
Varietal Denomination: Summer Star Baby

(71) Applicant: Nadine Widdowson, Dereham (GB)

(72) Inventor: Nadine Widdowson, Dereham (GB)

(73) Assignees: Floranova Ltd., Foxley, Dereham, Norfolk (GB); Genesis Plant Marketing Ltd., Langford, Maldon, Essex (GB)

( * ) Notice: Subject to any disclaimer, the term of this patent is extended or adjusted under 35 U.S.C. 154(b) by 0 days.

(21) Appl. No.: 15/932,556

(22) Filed: Mar. 13, 2018

(51) Int. Cl.
*A01H 5/02* (2018.01)

(52) U.S. Cl.
USPC ..... Plt./432
CPC ..... *A01H 5/02* (2013.01)

(58) Field of Classification Search
USPC ..... Plt./432
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Gaura* plant named 'Summer Star Baby', characterized by its compact, upright to broadly spreading plant habit; moderately vigorous growth habit; freely branching habit; freely flowering habit; light red purple-colored flowers; and good garden performance.

2 Drawing Sheets

Botanical designation: *Gaura lindheimeri.*
Cultivar denomination: 'SUMMER STAR BABY'.

BACKGROUND OF THE INVENTION

The present invention relates to a new and distinct cultivar of *Gaura* plant, botanically known as *Gaura lindheimeri* and hereinafter referred to by the name 'Summer Star Baby'.

The new *Gaura* is a product of a planned breeding program conducted by the Inventor in Foxley, United Kingdom. The objective of the breeding program is to create new semi-upright *Gaura* plants with attractive leaf and flower coloration.

The new *Gaura* plant originated from an open-pollination in July, 2006 in Foxley, United Kingdom of a proprietary selection of *Gaura lindheimeri* identified as code designation OSEXM, not patented, as the female, or seed, parent with an unknown selection of *Gaura lindheimeri* as the male, or pollen, parent. The new *Gaura* plant was discovered and selected by the Inventor as a single flowering plant from within the progeny of the stated open-pollination in a controlled environment in Foxley, United Kingdom in July, 2008.

Asexual reproduction of the new *Gaura* plant by vegetative tip cuttings in a controlled environment in Foxley, United Kingdom since September, 2008 has shown that the unique features of this new *Gaura* plant are stable and reproduced true to type in successive generations.

SUMMARY OF THE INVENTION

Plants of the new *Gaura* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Summer Star Baby'. These characteristics in combination distinguish 'Summer Star Baby' as a new and distinct *Gaura* plant:

1. Compact, upright to broadly spreading plant habit.
2. Moderately vigorous growth habit.
3. Freely branching habit.
4. Freely flowering habit.
5. Light red purple-colored flowers.
6. Good garden performance.

Plants of the new *Gaura* can be compared to plants of the female parent selection. Plants of the new *Gaura* differ from plants of the female parent selection in the following characteristics:

1. Plants of the new *Gaura* are more compact than plants of the female parent selection.
2. Flowers of plants of the new *Gaura* are darker red purple in color than flowers of plants of the female parent selection.
3. Plants of the new *Gaura* have shorter peduncles than plants of the female parent selection.

Plants of the new *Gaura* can be compared to plants of *Gaura lindheimeri* 'KLEGL06261', not patented. In side-by-side comparisons, plants of the new *Gaura* differ from plants of 'KLEGL06261' in the following characteristics:

1. Plants of the new *Gaura* have broader leaves than plants of 'KLEGL06261'.
2. Plants of the new *Gaura* have slightly larger flowers than plants of 'KLEGL06261'.
3. Flowers of plants of the new *Gaura* are brighter red purple in color than flowers of plants of 'KLEGL06261'.

Plants of the new *Gaura* can be compared to plants of *Gaura lindheimeri* 'Crimson Butterflies', disclosed in U.S. Plant Pat. No. 13,189. In side-by-side comparisons, plants of the new *Gaura* differ from plants of 'Crimson Butterflies' in the following characteristics:

1. Plants of the new *Gaura* are more compact than plants of 'Crimson Butterflies'.
2. Leaves of plants of the new *Gaura* are green in color whereas leaves of plants of 'Crimson Butterflies' are green to deep red in color.
3. Plants of the new *Gaura* have shorter peduncles than plants of 'Crimson Butterflies'.

Plants of the new *Gaura* can also be compared to plants of *Gaura lindheimeri* 'Florgaure', disclosed in U.S. Plant Pat. No. 26,518. In side-by-side comparisons, plants of the new *Gaura* differ from plants of 'Florgaure' in the following characteristics:

1. Plants of the new *Gaura* are more compact than plants of 'Florgaure'.
2. Leaves of plants of the new *Gaura* are green in color whereas leaves of plants of 'Florgaure' are dark green to brown in color.

BRIEF DESCRIPTION OF THE PHOTOGRAPHS

The accompanying colored photographs illustrate the overall appearance of the new *Gaura* plant showing the colors as true as it is reasonably possible to obtain in colored reproductions of this type. Colors in the photographs may differ slightly from the color values cited in the detailed botanical description which accurately describe the colors of the new *Gaura* plant.

The photograph on the first sheet is a side perspective view of a typical plant of 'Summer Star Baby' grown in a container.

The photograph on the second sheet is a close-up view of typical flowers of 'Summer Star Baby'.

DETAILED BOTANICAL DESCRIPTION

The aforementioned photographs and following observations, measurements and values describe plants grown during the late spring and early summer in 12-cm containers in an outdoor nursery in Boskoop, The Netherlands and under cultural practices typical of commercial *Gaura* production. During the production of the plants, day temperatures ranged from 15° C. to 28° C. and night temperatures ranged from 8° C. to 18° C. Plants were six months old when the photographs and description were taken. In the following description, color references are made to The Royal Horticultural Society Colour Chart, 2015 Edition, except where general terms of ordinary dictionary significance are used.

Botanical classification: *Gaura lindheimeri* 'Summer Star Baby'.

Parentage:

*Female, or seed, parent*.—Proprietary selection of *Gaura lindheimeri* identified as code designation OSEXM, not patented.

*Male or pollen parent*.—Unknown selection of *Gaura lindheimeri*, not patented.

Propagation:

*Type*.—By vegetative tip cuttings.

*Time to initiate roots, summer*.—About 10 to 16 days at temperatures about 20° C. to 23° C.

*Time to initiate roots, winter*.—About two to three weeks at temperatures about 20° C. to 23° C.

*Time to produce a rooted young plant, summer*.—About 30 to 35 days at temperatures about 20° C. to 23° C.

*Time to produce a rooted young plant, winter*.—About 35 to 40 days at temperatures about 15° C. to 18° C.

*Root description*.—Fine, fibrous; developing roots, close to 164D in color and older roots, close to 166D, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial; compact, upright to broadly spreading plant habit; broad inverted triangle to flattened globular in overall shape; freely basal branching habit with about 15 primary branches and about 46 secondary branches developing per plant, pinching enhances lateral branch development; dense and bushy plant form; moderately vigorous growth habit.

*Plant height, soil level to top of foliar plane*.—About 15.8 cm.

*Plant height, soil level to top of floral plane*.—About 22.2 cm.

*Plant diameter*.—About 39.5 cm.

Lateral branch description:

*Length*.—About 10.8 cm.

*Diameter*.—About 1.5 mm.

*Internode length*.—About 1.1 cm.

*Strength*.—Moderately strong; flexible.

*Aspect*.—Upright to horizontal.

*Texture and luster*.—Moderately to densely pubescent; moderately glossy.

*Color, developing*.—Close to 138B.

*Color, developed*.—Close to between 138B and 144B; upper surface strongly tinged with close to N186C and 187A.

Leaf description:

*Arrangement*.—Alternate, simple.

*Length*.—About 5.6 cm.

*Width*.—About 1.3 cm.

*Shape*.—Oblanceolate.

*Apex*.—Acute.

*Base*.—Narrowly cuneate.

*Margin*.—Entire; moderately to strongly undulate.

*Texture and luster, upper surface*.—Densely pubescent; slightly glossy.

*Texture and luster, lower surface*.—Densely pubescent; matte.

*Venation pattern*.—Pinnate.

*Color*.—Developing leaves, upper surface: Close to 143A. Developing leaves, lower surface: Close to 146A. Fully expanded leaves, upper surface: Close to 137B; older leaves moderately to strongly tinged with close to N186C; venation, close to 145A. Fully expanded leaves, lower surface: Close to between 143A and 146B; older leaves slightly to moderately tinged with close to 183A, 200B and 200C; venation, close to 146C.

*Petioles*.—Length: About 3 mm. Diameter: About 1.25 mm. Strength: Strong. Texture and luster, upper surface: Smooth, glabrous; margins, moderately to densely pubescent; matte. Texture and luster, lower surface: Moderately to densely pubescent; matte. Color, upper surface: Close to 145A; proximally, strongly tinged with close to 181A and 181B. Color, lower surface: Close to 146C; proximally, strongly tinged with close to 182B.

Flower description:

*Flower arrangement and habit*.—Single flowers arranged on terminal and axillary racemes; freely flowering habit with about 17 flowers per inflorescence; flowers face mostly outwardly to slightly upright.

*Fragrance*.—None detected.

*Natural flowering season*.—Plants flower continuously from late spring and throughout the summer in The Netherlands.

*Flower longevity*.—Individual flowers last about one week on the plant; flowers not persistent.

*Inflorescence height*.—About 10.7 cm.

*Inflorescence diameter*.—About 4.7 cm.

*Flower diameter*.—About 3.3 cm.

*Flower depth* (*height*).—About 2.9 cm.

*Flower buds*.—Length: About 1.7 cm. Diameter: About 3 mm. Shape: Oblong. Texture and luster: Moderately to densely pubescent; matte. Color: Close to between 63A and 185B.

*Petals*.—Arrangement: Four in a single whorl. Length: About 2 cm. Width: About 1 cm. Shape: Obovate, slightly concave. Apex: Acute. Base: Acuminate. Margin: Entire. Texture and luster, upper and lower surfaces: Smooth, glabrous; moderately velvety; matte. Color: When opening, upper and lower surfaces: Close to 68A; distally, close to 68B; venation, close to 67B. Fully opened, upper and lower surfaces: Close to 68A; venation, close to 67B; color becoming closer to 61B with development.

*Sepals*.—Arrangement: Four in a single whorl. Length: About 1.7 cm. Width: About 1.5 mm. Shape: Lanceolate; strongly reflexed. Apex: Narrowly acute. Base: Broadly cuneate. Margin: Entire. Texture and luster, upper surface: Smooth, glabrous; margins, moderately pubescent; matte. Texture and luster, lower surface: Moderately pubescent; matte. Color, upper surface: Close to 53D. Color, lower surface: Close to 63A.

*Peduncles*.—Length: About 9.5 cm. Diameter: About 1.5 mm. Strength: Strong. Aspect: Mostly upright. Texture and luster: Sparsely to moderately pubescent; moderately glossy. Color: Close to between 138B and 144B; upper surface strongly tinged with close to N186C and 187A.

*Pedicels*.—Length: About 7 mm. Diameter: About 1 mm. Strength: Moderately strong. Aspect: About 15° from peduncle axis. Texture and luster: Smooth, glabrous; glossy. Color: Close to 200A.

*Reproductive organs*.—Stamens: Quantity: Eight per flower. Filament length: About 1.3 cm. Filament color: Close to NN155D. Anther shape: Oblong. Anther length: About 2 mm. Anther diameter: About 0.5 mm. Anther color: Close to 187A. Pollen amount: Scarce to moderate. Pollen color: Close to 4C. Pistils: Quantity: One per flower. Pistil length: About 2 cm. Style length: About 1.9 cm. Style color: Close to 68C; proximally, close to N155B. Stigma shape: Three-parted. Stigma size: About 1 mm by 2 mm. Stigma color: Close to 4C. Ovary color: Close to 200A. Seeds and fruits: Seed and fruit development have not been observed on plants of the new *Gaura* to date.

Garden performance: Plants of the new *Gaura* have been observed to have good garden performance and tolerate wind, rain and temperatures ranging from about −18° C. to about 35° C. and to be suitable for USDA Hardiness Zones 6 to 10.

Pathogen & pest resistance: To date, plants of the new *Gaura* have not been observed to be resistant to pathogens and pests common to *Gaura* plants.

It is claimed:

1. A new and distinct *Gaura* plant named 'Summer Star Baby' as illustrated and described.

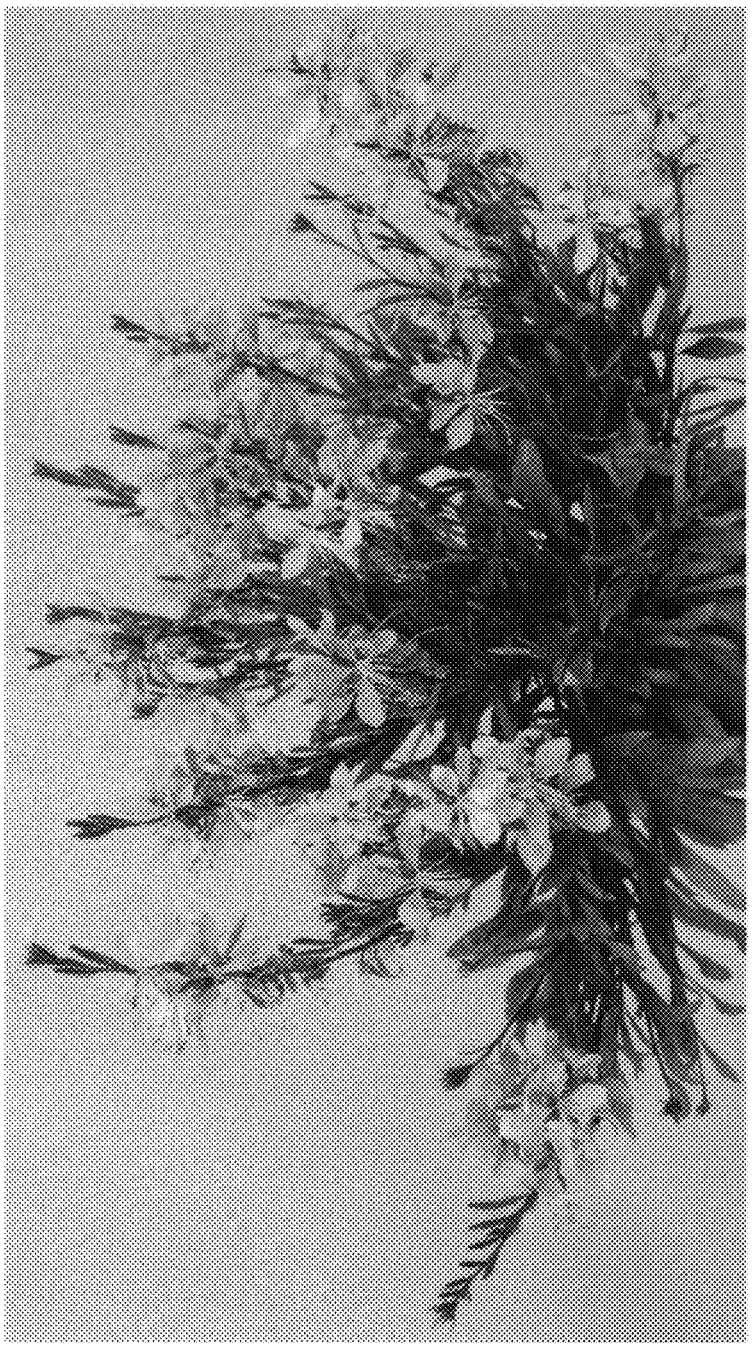

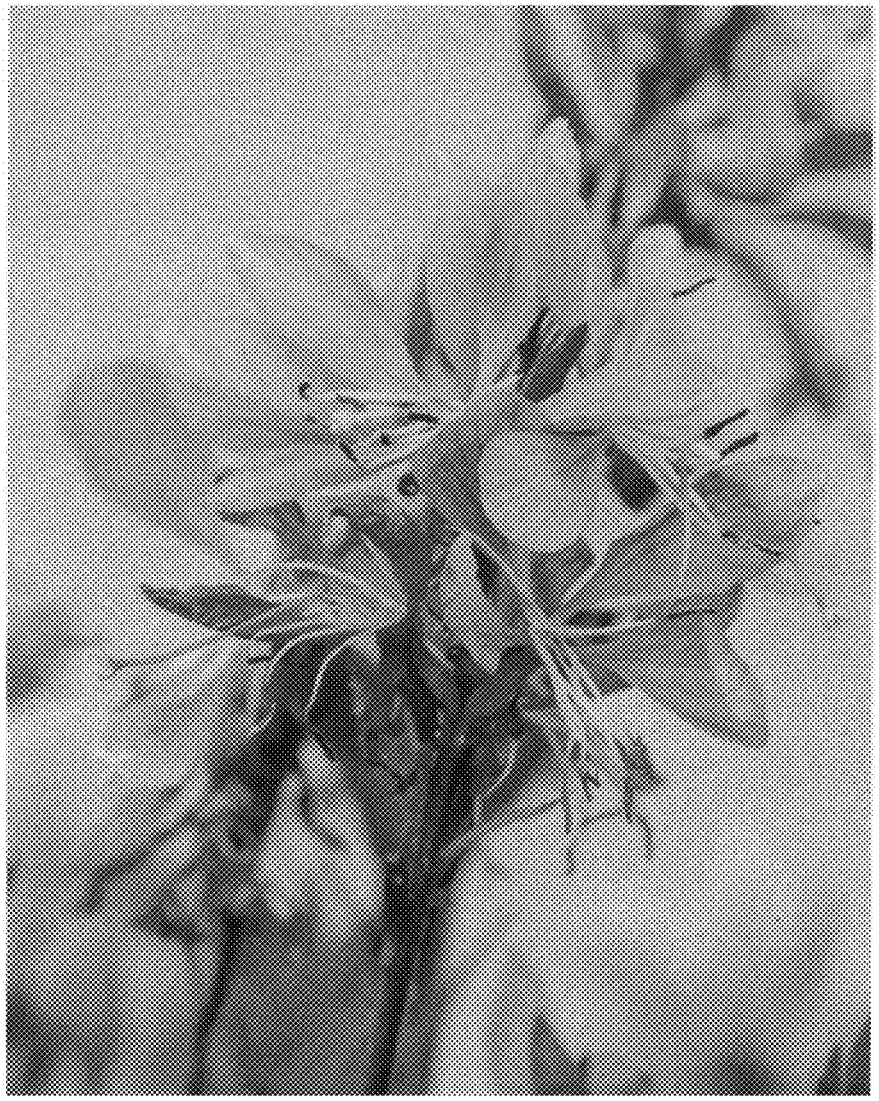

* * * * *